United States Patent

Hogan

[11] Patent Number: 5,961,494
[45] Date of Patent: Oct. 5, 1999

[54] MARKING SYRINGE

[76] Inventor: Thomas Hogan, 2420 Westport Cir., Marietta, Ga. 30064

[21] Appl. No.: 08/883,268

[22] Filed: Jun. 26, 1997

[51] Int. Cl.⁶ .................................................. A61M 5/00
[52] U.S. Cl. ......................... 604/191; 604/223; 606/116; 81/9.22
[58] Field of Search ................... 604/191, 181, 604/187, 116, 61, 207, 208–211, 223, 224, 115, 218, 130; 222/137, 391, 327, 82, 129, 135; 81/9.22; 606/116, 117; 128/DIG. 6

[56] References Cited

U.S. PATENT DOCUMENTS

| | | |
|---|---|---|
| 3,949,746 | 4/1976 | Wallach . |
| 4,152,412 | 5/1979 | Brewer . |
| 4,214,490 | 7/1980 | Chizek . |
| 4,726,594 | 2/1988 | Benke . |
| 5,135,507 | 8/1992 | Haber et al. ............................ 604/110 |
| 5,147,307 | 9/1992 | Gluck . |
| 5,192,270 | 3/1993 | Carswell, Jr. . |
| 5,326,001 | 7/1994 | Holmquist et al. . |
| 5,376,079 | 12/1994 | Holm ....................................... 604/209 |
| 5,591,135 | 1/1997 | Sullivan .................................. 604/208 |

Primary Examiner—Ronald Stright
Attorney, Agent, or Firm—William B. Dyer III, Esq.; Troutman Sanders LLP

[57] ABSTRACT

A marking syringe which allows an individual using the syringe to inject a fluid such as a vaccine into an animal and, at the same time, mark the location of the injection on the animal. More specifically, the marking syringe includes a vaccine syringe and an ink syringe connected to a handle. Activation of the handle simultaneously activates the vaccine syringe and the marking syringe. The vaccine syringe and the ink syringe are respectively connected to a source of vaccine and a source of ink. After connection to the vaccine and ink sources, the syringe needle is inserted into the animal and a syringe handle is actuated. As the handle is actuated, a vaccine syringe and an ink syringe both discharge their contents. The position of the ink syringe relative to the vaccine syringe is such that the discharged ink marks the animal in the approximate location of the vaccine injection.

6 Claims, 1 Drawing Sheet

MARKING SYRINGE

FIELD OF THE INVENTION

This invention relates in general to devices for injecting medicines into animals and, more particularly, to devices which mark the animal concurrently upon injecting the animal.

BACKGROUND OF THE INVENTION

The days of farmers independently operating small family farms profitably are, for the most part, a distant memory. Today's successful farmers rely heavily on quantity, quality and efficiency to operate their businesses successfully. In the hog industry, for example, a successful business operation may include hundreds, if not thousands, of hogs. In such an operation, overhead is kept low by employing only a handful of people to perform all aspects of the maintenance of the hogs, including breeding, feeding, treating, and selling.

The recognized need to increase efficiency in the hog production industry has given rise to the development of numerous devices for assisting hog farming operations. Computers are heavily used to track information related to genetics, feed consumption, and environmental factors, often providing feedback information concerning the quality of the final product. Such feedback allows a farmer to modify production processes for better outcomes. The efforts of farmers to increase profitability and productivity have also been assisted by both the pharmaceutical and nutrition industries. Each of these industries has produced a vast array of nutrition supplements and medicinal regimens to keep hogs healthier and, ultimately, more valuable. The negative aspect of these new regimens is that they require increased man-hours to administer.

For instance, it is not uncommon for each hog in a herd to require 7–9 medicinal injections per year—which is nearly double the number required only a decade ago. In today's hog farming environment, both the number of injections per hog and the number of hogs in a typical operation are increasing at the same time the number of employees on hand to maintain the hogs is decreasing. Thus, the maximization of personnel resources and delivery methods becomes ever more critical.

Aside from sheer volume, the delivery of injectible medicines to animals is complicated by the temperaments and behavior of the animals themselves. As a rule, hogs are generally not pleased at the prospect of receiving injections. Furthermore, there is no practical way to restrict movement of the hogs during the injection process. As a result, a hog who is about to receive or has received his medicine may be difficult to control and may intermingle with hogs who have not yet been injected. Accordingly, the possibility exists that certain hogs may go without their intended injections while others mistakenly receive multiple doses. Either scenario-leaving an animal unvaccinated or overvaccinating an animal—carry significant downfalls. Such mistakes in the administration of medicines could, in one extreme, threaten the well-being of the animals. In another extreme, the result may be toxic levels of medicines in the end products.

Various methods and devices have been developed to combat these inefficiencies, although recent changes to industry standards and production methods for hogs have rendered many of these solutions obsolete. For instance, as recently as twenty years ago it was a standard practice for farmers to deliver injectible medicines without paying particular attention to the specific location of the injections, either on the hogs or relative to one another. Subsequent research has indicated that this practice resulted in problems such as the delivery of medicines to areas to which they were not optimally assimilated into the bloodstream of the hog. Just as bad, delivery of the medicines to a disadvantageous location could blemish or damage the surrounding tissue, thereby devaluating the final meat product.

A good example of an early medicine delivery device which manifested the above referenced problems can be found in U.S. Pat. No. 3,949,746 (the '746 patent) issued to Wollach. The medicine delivery device of the '746 patent comprises a hypodermic syringe apparatus and includes a contact member having an apertured front plate and a hydraulic cylinder reciprocated mounting plate supporting a group of hypodermic needles in slidable registry with the front plate openings. The needles pierce a liquid absorbing web backing the front plate. Each needle is connected by a flexible tube to an adjustable stroke piston pump and then to liquid injectible holding receptacles. The pistons are simultaneously actuated by a motor driven cam carrying shaft. The motor is controlled by a handle carried switch to rotate the shaft one turn. The shaft carrying cam also controls the flow of the liquid to the handle cylinder, and the absorbent pad is connected to a source of antiseptic. A marking pad is carried by the handle front wall to identify the puncture area.

Because of the complicated nature and resulting expense of the device of the '746 patent, it never found widespread use in the livestock industry, where profit margins are typically too low to support either the purchase or the continued maintenance required by such a complicated device. Additionally, the manner in which the injections are delivered by the '746 patent is now considered unacceptable for several reasons. First, livestock experts now agree that delivering a large number of treatments in essentially the same location may limit the effectiveness of some medicines and may even be detrimental to the animal. Secondly, the former practice of delivering injectible treatments to "high yield" meat areas such as the rump (as shown in the '746 patent) reduces the quality of the salable meat from that area and reduces the profitability of the animal.

More recently, individual syringes have been developed which allow the farmer to apply an injection in any desired location using a singlehandled manual syringe. One such syringe is the "Easy Vac" Automatic Syringe, manufactured by Forlong & Massey d/b/a Instrument Supplies of New Zealand and distributed in the United States by Vac-Pac Incorporated of Marietta, Ga. (1-800-793-1671). Typically, the Instrument Supplies Easy-Vac syringe is used in conjunction with a so-called "paint stick". In livestock operations, the paint stick is a well known device which resembles a large grease pencil and is used to mark the hog which has received the injection. If used properly, the farmer injects the animal with a syringe held in one hand and marks the injected animal with a paint stick held in the other hand. Proper use of the paint stick identifies the animal as one which has been injected. This method does not necessarily provide a visible indication of the location of the injection.

Even this improved method of delivering injections poses serious problems for the farmer. First, it is extremely easy for a low-paid manual laborer who is delivering the injections to take a shortcut by injecting the animal in an easily accessible but improper area (such as the rump), then use the paint stick to mark the animal where the injection should have been given, such as in the neck. Secondly, even if used properly, both of the hands of the farmer are occupied, making it extremely difficult to control the animal in any meaningful way. Often, an animal will escape control of the farmer after being injected and before being marked, resulting in the potential risk of an animal receiving multiple injections, or not receive an injection at all.

Accordingly, a need exists for an apparatus for injecting hogs and other livestock which delivers injections easily, accurately and reliably. There is an additional need for such an apparatus which will mark both the animal injected and the location of the injection on the animal concurrent with the delivery of the injection. Finally, there exists a need for such an apparatus which can be operated with one hand, leaving the farmer one hand free to control the animal, protect himself or deliver a second injection and mark with a second apparatus substantially simultaneously.

SUMMARY OF THE INVENTION

The present invention is a marking syringe which allows an individual using the marking syringe to inject a fluid such as a vaccine into an animal and, at the same time, mark the location of the injection on the animal and the animal being injected. More specifically, the marking syringe of the present invention include a vaccine syringe and an ink syringe which are respectively connected to a source of vaccine and a source of ink. A syringe handle is operatively connected to both the vaccine syringe and the ink syringe. After connection to the vaccine and ink sources, the syringe needle is inserted into the animal and the syringe handle is actuated. As the handle is actuated, the vaccine syringe and the ink syringe both simultaneously discharge their contents. The position of the ink syringe relative to the vaccine syringe is such that the discharged ink marks the animal in the approximate location of the vaccine injection through the needle.

The marking syringe of the present invention carries many advantages over current injecting and marking systems. First, because the handle activates both the vaccine syringe and the marking syringe simultaneously, the marking syringe of the present invention can be easily operated with one hand, leaving the user's other hand free to control the animal or to operate a second marking syringe. The operation of a second syringe poses obvious advantages, in that one user could apply twice as many injections in roughly the same amount of time, thereby cutting in half the number of man-hours needed to accomplish the task.

Another advantage of the marking syringe of the present invention is that it applies a mark to the animal in close proximity to the actual injection by the needle. Unlike current popular methods of marking, the user cannot apply the injection with the needle in one area of the animal and apply the mark to a different area.

Yet another advantage the marking syringe of the present invention is its simplicity of use. Specifically, the marking syringe of the present invention does not require power of any type and, thus, can be easily used in remote locations. Additionally, the marking syringe of the present invention is easily disassembled for cleaning or replacement of failed parts.

Accordingly, it is an object of the present invention to provide an apparatus for injecting hogs and other livestock which delivers injections easily, accurately and reliably. It is another object of the present invention to provide an apparatus which will mark both the animal injected and the location of the injection on the animal concurrent with the delivery of the vaccine injection. It is yet another object of the present invention to provide an apparatus which can accomplish the foregoing and be operated with one hand, leaving the user one hand free to control the animal, protect himself or deliver a second injection and mark with a second apparatus substantially simultaneously.

DETAILED DESCRIPTION

Figure 1:
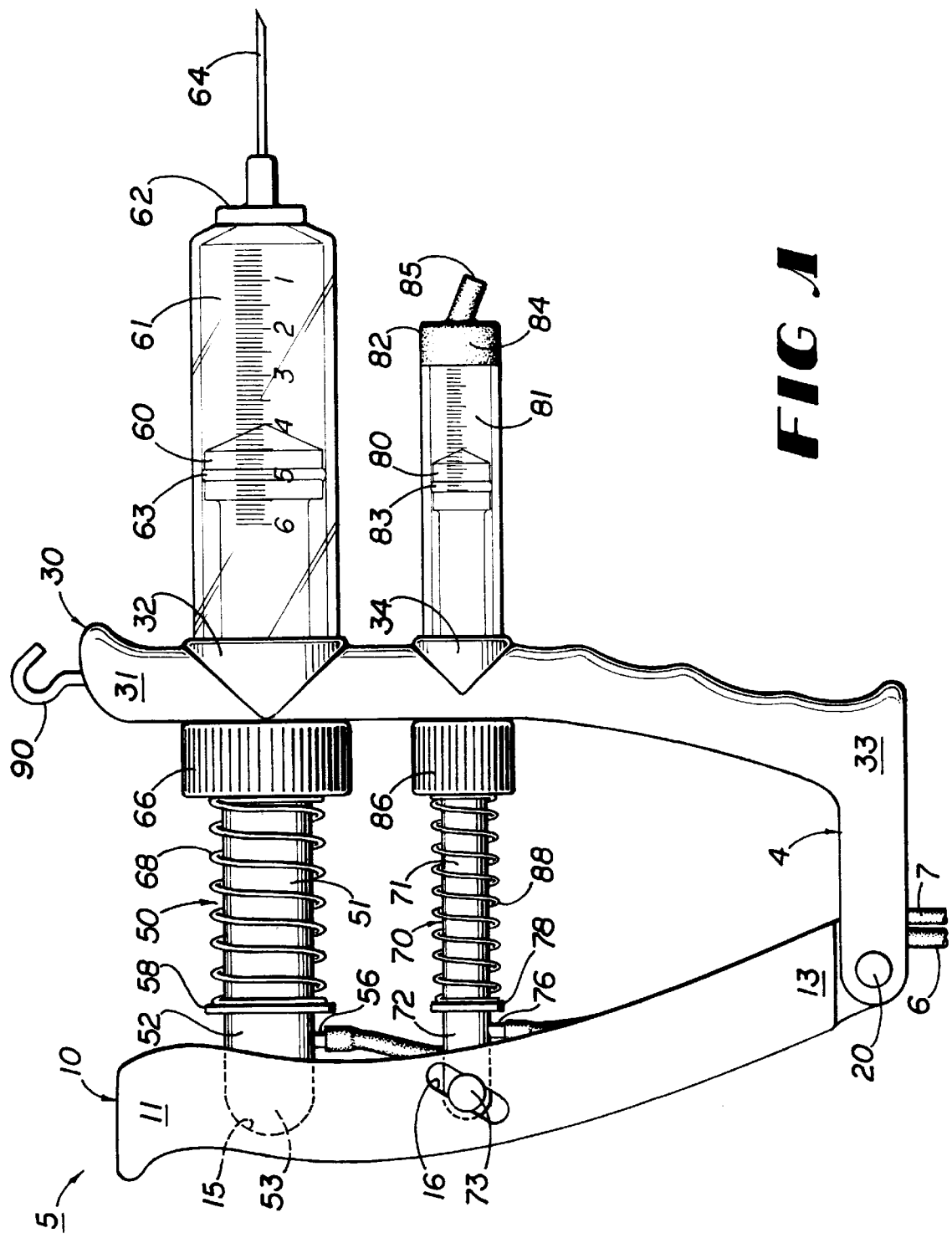
FIG. 1 is an illustration of an exemplary embodiment of the present invention in a typical operating environment.

Referring now to the drawings, FIG. 1 is an illustration of a preferred embodiment of the present invention, which shows a marking syringe for simultaneously injecting a vaccine or other substance into an animal while placing an identifying mark on the animal in the vicinity of the injection.

As can be seen in FIG. 1, the marking syringe 5 comprises, generally, a syringe handle 4 operatively connected to a vaccine syringe 50 and an ink syringe 70. The syringe handle 4 comprises a first syringe handle 10 pivotally connected to a second syringe handle 30. The first syringe handle 10 is elongated, having a first end 11 and a second end 13. The handle 10 is generally shaped for comfortable receipt into the palm portion of the hand of the user. A socket 15 is located adjacent the end 11, and a slot 16 is located between the socket 15 and the end 13. The handle 10 has a pivot hole at its second end 13.

The second syringe handle 30 of marking syringe 5 is also elongated and has a first end 31 and a second end 33. The first end 31 of the second syringe handle 30 securely receives a hook 90 for storage of the marking syringe 5 between uses. The second syringe handle 30 is configured to fit as a finger grip for the user. The second end 33 of the second syringe handle 30 is sized to slidably straddle the second end 13 of the first handle 10 and has a pivot hole through its thickness. The second handle 30 includes integral vaccine syringe collar 32 and integral ink syringe collar 34.

During assembly, the second end 33 of the second syringe handle 30 is positioned over the second end 13 of the first syringe handle 10 such that the pivot holes in the ends 13 and 33 are axially aligned. Thereafter, pivot pin 20 is inserted through the aligned holes and appropriately secured therein in any number of ways, including deforming distal ends of pivot pin 20 so that the diameter of the pivot pin 20 is larger at the points of deformation than the diameter of the pivot pin receiving holes, thereby preventing withdrawal of pivot pin 20 through the pivot pin receiving holes. After the pivot pin is properly positioned and secured, the second syringe handle 30 rotates about the axis of pivot pin 20 in a plane defined by second syringe handle 30 and first syringe handle 10. In use, the first and second handles 10 and 30 are initially in a spread position. The user can then grip the first and second handles 10 and 30 and squeeze them into a closed position as the handles 10 and 30 pivot about the pin 20.

The vaccine syringe 50 is mounted between the handles 10 and 30 by means of the collar 32 on handle 30 and the socket 15 on handle 10. The vaccine syringe 50 comprises a vaccine syringe head 52 with a ball 53, an extendible vaccine syringe shaft 51, vaccine syringe biasing spring 68, vaccine syringe plunger 60, vaccine dosage chamber 61, vaccine syringe needle fastener 62, and a needle 64. In order to connect the syringe 50 to the handle 4, the dosage chamber 61 is threaded into the handle collar 32 of handle 30, and the vaccine syringe head 52 is connected to the handle 10 by engaging the ball 53 of the head 52 into the socket 15 of the handle 10.

The head 52 is hollow and comprises the ball 53 for attaching the head 52 to the handle 10, a vaccine syringe nipple 56, and a spring stop 58. The vaccine syringe nipple 56 is integral to the hollow vaccine syringe head 52 and is sized to securely receive a syringe vaccine hose 6. Vaccine is delivered to the hollow interior cavity of the head 52 via vaccine hose 6 which is connected to a vaccine source (not shown). The vaccine syringe spring stop flange 58 extends laterally about the periphery of the vaccine syringe head 52.

The extendible vaccine syringe shaft 51 interconnects the syringe head 52 and the plunger 60. The shaft 51 has an interior axial conduit (not shown) which communicates a one end to the interior cavity of the head 52 and at the other end to an interior axial conduit (not shown) through the plunger 60. The syringe shaft 51 extends through a vaccine syringe collar 32 of the second syringe handle 30 and into the vaccine dosage chamber 61. In order to vary the amount of dosage, the shaft 51 has a vaccine dosage adjust valve 66. The dosage adjust valve 66 comprises a collar that engages the plunger 60 on one end and is threaded onto shaft 51.

The vaccine syringe plunger 60 slides within vaccine dosage chamber 61. An O-ring 63 creates a liquid tight seal between the periphery of plunger 60 and the interior wall of the dosage chamber 61. The plunger 60 has a check valve (not shown) within its interior axial conduit that allows liquid to pass only in the direction toward the needle end of the syringe 50.

The vaccine dosage chamber 61 is formed of a translucent or transparent material and is secured at its first end to the vaccine syringe collar 32. Vaccine dose chamber 61 may be scored with incremental graduations to assist a user in dosage measurements. At its second end, the vaccine dosage chamber 61 removably receives a vaccine syringe needle fastener 62. The vaccine syringe needle fastener 62 is fitted to capture a needle 64. A check valve (not shown) is fitted within the needle fastener 62 to allow liquid flow only out of the needle.

A vaccine syringe biasing spring 68 is disposed around the vaccine syringe shaft 51 between the vaccine syringe stop flange 58 and the vaccine dosage adjust valve 66. The biasing spring 68 is a compression spring which serves to return the handles 10 and 30 to their initial spread position after being squeezed closed by the user.

When the handles 10 and 30 are squeezed together, the plunger 60 moves within the dosage chamber 61. The movement of the plunger closes the check valve within the plunger 60 to force vaccine in the dosage chamber 61 through the check valve within the needle fastener 62 and out through the needle 64. When the handles 10 and 30 are released by the user, the check valve within the needle fastener 62 closes to preclude fluid or air being drawn into the dosage chamber 61 through the needle 64. Simultaneously, the check valve within the plunger 60 opens so that vaccine is drawn into dosage chamber 61 through the nipple 56, the hollow head 52, the conduit within the shaft 51, and the conduit with the plunger 60. By turning the dosage adjust valve 66, the length of the shaft 51 is changed. Changing the length of the shaft 51 changes the length of the plunger stroke, and the amount of medicine delivered through the needle 64 is accordingly changed.

Similarly, the ink syringe 70 is mounted between the handles 10 and 30 by means of the collar 34 on handle 30 and the slot 16 on the handle 10. The ink syringe 70 comprises a ink syringe head 72 with a pin 73 extending therefrom, an extendible ink syringe shaft 71, ink syringe biasing spring 88, ink syringe plunger 80, ink dosage chamber 81, and an ink discharge orifice 82. In order to connect the syringe 70 to the handle 4, the dosage chamber 81 is threaded into the handle collar 34 of handle 30, and the ink syringe head 72 is connected to the handle 10 by engaging the pin 73 of the head 72 into the slot 16 of the handle 10. The combination of the slot 16 and pin 73 assures axial alignment of the plunger 80 with the ink dosage chamber 81.

The head 72 is hollow and comprises the pin 73 for attaching the head 72 to the handle 10, an ink syringe nipple 76, and a spring stop 78. The ink syringe nipple 76 is integral to the hollow ink syringe head 72 and is sized to securely receive a syringe ink hose 7. Ink is delivered to the hollow interior cavity of the head 72 via ink hose 7 which is connected to a ink source (not shown). The ink syringe spring stop flange 78 extends laterally about the periphery of the ink syringe head 72.

The extendible ink syringe shaft 71 interconnects the syringe head 72 and the plunger 80. The shaft 71 has an interior axial conduit (not shown) which communicates a one end to the interior cavity of the head 72 and at the other end to an interior axial conduit (not shown) through the plunger 80. The syringe shaft 71 extends through a ink syringe collar 34 of the second syringe handle 30 and into the ink dosage chamber 81. In order to vary the amount of ink dispensed, the shaft 71 has a ink dosage adjust valve 86. The dosage adjust valve 86 comprises a collar that engages the plunger 80 on one end and is threaded onto shaft 71.

The ink syringe plunger 80 slides within ink dosage chamber 61. An O-ring 83 creates a liquid tight seal between the periphery of plunger 80 and the interior wall of the dosage chamber 81. The plunger 80 has a check valve (not shown) within its interior axial conduit that allows liquid to pass only in the direction toward the needle end of the syringe 70.

The ink dosage chamber 81 is formed of a translucent or transparent material and is secured at its first end to the ink syringe collar 34. Ink dose chamber 81 may be scored with incremental graduations to assist a user in dosage measurements. At its second end, the ink dosage chamber 81 has the discharge orifice 82. A check valve (not shown) is fitted within the discharge orifice 82 to allow ink flow only out of the discharge orifice 82. The discharge orifice has a body portion 83 and an end portion 85 which is set at angle to axis of the cylindrical dosage chamber 81. By rotating the discharge orifice on the cylindrical dosage chamber 81, the end portion may be aimed and thereby control the location of the resulting mark with respect to the needle 64.

An ink syringe biasing spring 88 is disposed around the ink syringe shaft 71 between the ink syringe stop flange 78 and the ink dosage adjust valve 86. The biasing spring 88 is a compression spring which serves to return the handles 10 and 30 to their initial spread position after being squeezed closed by the user.

When the handles 10 and 30 are squeezed together, the plunger 80 moves within the dosage chamber 81. The movement of the plunger closes the check valve within the plunger 80 to force ink in the dosage chamber 81 through the check valve within the discharge orifice 82 and out through the discharge orifice 82. When the handles 10 and 30 are released by the user, the check valve within the discharge orifice 82 closes to preclude fluid or air being drawn into the dosage chamber 81 through the discharge orifice 82. Simultaneously, the check valve within the plunger 80 opens so that ink is drawn into dosage chamber 81 through the nipple 76, the hollow head 72, the conduit within the shaft 71, and the conduit with the plunger 80. By turning the dosage adjust valve 86, the length of the shaft 71 is changed. Changing the length of the shaft 71 changes the length of the plunger stroke, and the amount of ink delivered through the discharge orifice 82 is accordingly changed.

In operation, an appropriately sized needle 64 is selected and received within vaccine syringe needle fastener 62. Automatic syringe vaccine hose 6 and syringe ink hose 7 are connected to their respective vaccine and ink sources. Next, the vaccine dose adjust valve 66 and the ink dose adjust valve 86 are rotated to achieve proper dosing. As each of the respective adjust valves is rotated, the functional connection between the adjust valves and their respective syringe shafts moves the initial position of the respective syringe plungers to determine dosage amounts. When adjusted according to dosing requirements, first syringe handle 10 is rotated about pivot pin 20 toward second syringe handle 30 to clear air from the respective hoses and prime the respective syringes.

Actuation of the first syringe handle 10 in such a fashion forces both the vaccine syringe shaft 51 and the ink syringe shaft 71 forward. As a result, both the vaccine syringe plunger 60 and ink syringe plunger 80 move toward the needle 64 and ink discharge orifice 82, respectively, thereby forcing substantially simultaneous expulsion of the contents of the vaccine dose chamber 61 and ink dose chamber 81. As the first syringe handle 10 is compressed, vaccine syringe biasing spring 68 and ink syringe biasing spring 88 are similarly compressed. Following completion of full compression of the first syringe handle 10 and subsequent release of same, compressed biasing springs 68 and 88 return the first syringe handle 10 to its original position.

The method of movement of vaccine and ink into their respective dosage chambers 61 and 81 is accomplished by any number of devices well known to those skilled in the art of syringes. For instance, an exemplary embodiment of the marking syringe 5 incorporates hollow vaccine and ink shafts 51 and 71 and unidirectional diaphragms or check valves within the respective plungers 60 and 80 and the respective needle fastener 62 and discharge orifice 82. After actuation of the first syringe handle 10 and injection of vaccine and ink, the return of the first syringe handle 10 to its original position by the respective biasing springs 68 and 88 creates a vacuum within the respective dosage chambers. The respective unidirectional diaphragms open and close as previously described under this circumstance to draw either vaccine or ink into its dosage chamber. As the first syringe handle reaches its initial position, the respective dosage chambers 61 and 81 are filled with their intended contents and the diaphragm closes, thereby allowing pressurized expulsion of the chamber contents upon actuation of the first syringe handle as previously described.

While the invention has been described in detail with respect to specific embodiments thereof, it will be appreciated that those skilled in the art, upon attaining an understanding of the foregoing, may readily conceive of alterations to, variations of and equivalents to these embodiments. Accordingly, the scope of the present invention should be assessed as that of the appended claims and any equivalents thereto and not limited to the specific embodiments articulated hereinabove.

I hereby claim:

1. A marking syringe, for simultaneously vaccinating an animal and applying an indicator mark in the general vicinity of the site of the vaccination, said marking syringe comprising:

a vaccine syringe including a needle for injecting a vaccine into the animal at a particular site;

a marking agent applicator including a discharge orifice for discharging a marking agent onto the exterior of the animal in the general vicinity of said particular site;

a marking syringe handle carrying said vaccine syringe and said marking agent applicator, and an actuator carried by said marking syringe handle for simultaneously activating both said vaccine syringe and said marking agent applicator.

2. The marking syringe of claim 1, wherein said discharge orifice is adjustable to deposit marking agent at a position immediately adjacent said particular site.

3. The marking syringe of claim 1, wherein said vaccine syringe further includes a connection to a vaccine source.

4. The marking syringe of claim 1, wherein said marking agent applicator further includes a connection to a marking agent source.

5. A marking syringe, for simultaneously vaccinating an animal and applying an indicator ink spot in the general vicinity of the site of the vaccination, said marking syringe comprising:

a vaccine syringe including:
  a vaccine syringe head disposed to receive vaccine from a vaccine source;
  a vaccine plunger having a vaccine plunger shaft extending from said syringe head, said vaccine plunger shaft including a vaccine channel disposed to receive vaccine from said vaccine syringe head;
  a vaccine dosage chamber receiving said vaccine plunger and for receiving vaccine from said vaccine source through said vaccine channel; and
  a needle extending from said vaccine dosage chamber for dispensing vaccine from said vaccine dosage chamber into the animal;

an ink syringe including:
  an ink syringe head disposed to receive ink from an ink source;
  an ink plunger having an ink plunger shaft extending from said ink syringe head, said ink plunger shaft including an ink channel disposed to receive ink from said ink syringe head;
  an ink dosage chamber for receiving said ink plunger and for receiving ink from an ink source through said ink channel; and
  a discharge orifice extending from said ink dosage chamber for dispensing ink from said ink dosage chamber onto the skin of the animal; and a handle for capturing said vaccine syringe and said ink syringe and for simultaneously activating both the vaccine syringe and the ink syringe, said handle comprising:
  a first handle portion for capturing said vaccine syringe and said ink syringe; and
  a second handle portion for simultaneously actuating said vaccine syringe and said ink syringe, said second handle portion being connected to said vaccine syringe head and said ink syringe head.

6. The marking syringe of claim 5, wherein said second handle portion includes a slot and said ink syringe includes a pin, said slot and pin being engagable to facilitate movement of said second handle portion without mechanical conflict with said ink syringe.

* * * * *